United States Patent [19]
Greve et al.

[11] 3,950,383
[45] Apr. 13, 1976

[54] CYANOALKYLAMINO-AMIDO BENZOPHENONES

[75] Inventors: Heinz Günter Greve; Klaus Resag, both of Frankfurt am Main, Germany

[73] Assignee: Cassella Farbwerke Mainkur Akt, Frankfurt am Main, Germany

[22] Filed: Nov. 5, 1974

[21] Appl. No.: 521,010

Related U.S. Application Data
[63] Continuation-in-part of Ser. No. 358,455, May 8, 1975, Pat. No. 3,888,899.

[52] U.S. Cl............................. 260/465 D; 424/304
[51] Int. Cl.² ...................................... C07C 121/78
[58] Field of Search ............................... 260/465 D

[56] References Cited
UNITED STATES PATENTS
3,772,371    11/1973    Tachikawa et al.............. 260/465 X

*Primary Examiner*—Lewis Gotts
*Assistant Examiner*—Dolph A. Torrence
*Attorney, Agent, or Firm*—Francis M. Crawford

[57] ABSTRACT

The present invention relates to pharmacologically valuable new benzophenone derivatives having a pronounced sedative action on the central nervous system and some of which also possess muscle-relaxing and aggression-inhibiting properties. These new derivatives have the structural formula

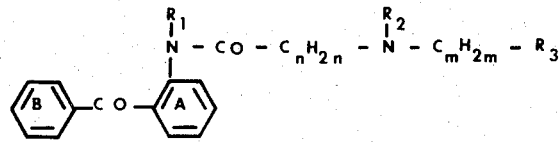

and their addition salts, in which
$R_1$ and $R_2$ are substituents selected from the group consisting of hydrogen, alkyl having 1–5 carbon atoms, alkenyl having 2 to 4 carbon atoms, alkinyl having 2 to 4 carbon atoms or β-bromoallyl ($-CH_2-CBr = CH_2$) ; $R_3$ is $-CN$; $n$ is an integer selected from 1 and 2; and $m$ is an integer selected from 1, 2 and 3, wherein the rings A and B may be substituted, ring A being substituted preferably with a halogen such as chlorine or with nitro, trifluoromethyl, methyl, methoxy or methylmercapto, preferably in the 5 position, and ring B being preferably substituted in the 2' position with chlorine or fluorine. The radical $R_1$ preferably signify hydrogen or a methyl, ethyl or propargyl group, the radicals for $R_2$ preferably signify hydrogen or a methyl, allyl or an n-butyl group.

C compounds represented by the above structural formula may be produced by reacting a compound represented by the formula

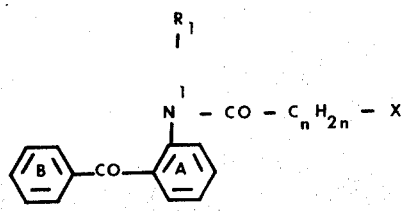

with a compound having the formula $Y - C_mH_{2m}- R_3$, one of X and Y signifying the substituent $R_2 - NH$ — and the other signifying a halogen atom, preferably a bromine or chlorine atom, so as to form the above specified benzophenone derivative with the elimination of H — Hal, $R_1$, $R_2$, $R_3$, $n$ and $m$ being as defined above, and the rings A and B being optionally substituted as discussed above. The hydrogen halide which is eliminated is advantageously bound by the addition of an acid-binding agent, as for example, a molar excess of the amine used in the reaction or, for example, triethylamine, dimethylaniline, potassium or sodium carbonate or sodium bicarbonate. The reaction is carried out in a suitable solvent, preferably at an elevated temperature, typically the reflux temperature of the solvent used.

8 Claims, No Drawings

CYANOALKYLAMINO-AMIDO BENZOPHENONES

This is a continuation-in-part application of U.S. patent application Ser. No. 358,455 filed May 8, 1975, now U.S. Pat. No. 3,888,899.

The invention relates to pharmacologically valuable new benzophenone derivatives of the general formula I

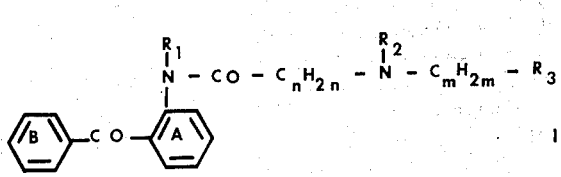

and their acid addition salts, in which $R_1$ and $R_2$ signify hydrogen or an alkyl radical with 1 to 5 carbon atoms, an alkenyl radical with 2 to 4 carbon atoms, an alkinyl radical with 2 to 4 carbon atoms, or a $\beta$-bromoallyl radical ($-CH_2-CBr=CH_2$);

$R_3$ signifies a $-CN$;

$n$ is 1 or 2;

$m$ is 1, 2 or 3 and the rings A and B may be substituted.

Preferred substituents for the ring A are halogen, especially chlorine, nitro, trifluoromethyl, methyl, methoxy or methylmercapto, and substitution is preferably in the 5 position, and preferred substituents for the ring B are fluorine or chlorine, substitution preferably being at the 2' position. The radical $R_1$ preferably signifies hydrogen or a methyl, ethyl or propargyl group, the radical $R_2$ preferably signifies hydrogen, a methyl, allyl or an n-butyl group.

Compounds of the general formula I may be produced by reacting a benzophenone derivative of the general formula

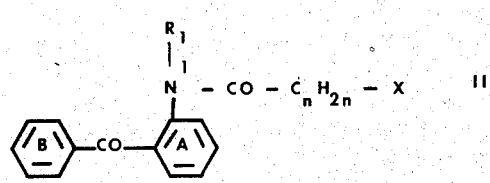

with a compound of the general formula III $$Y - C_mH_{2m} - R_3 \qquad \text{III}$$

one of X and Y signifying the radical $R_2-NH-$ and the other signifying a halogen atom, preferably a bromine or chlorine atom, so as to form a compound of the general formula I with the elimination of H—Hal, $R_1$, $R_2$, $R_3$, $n$ and $m$ being ad defined above, and the rings A and B being optionally substituted as discussed above. The hydrogen halide which is eliminated is advantageously bound by the addition of an acid-binding agent. Suitable acid-binding agents are a molar excess of the amine used in the reaction or, for example, triethylamine, dimethylaniline, potassium or sodium carbonate or sodium bicarbonate. The amine can also be employed in the form of an acid addition salt, in which case it is then necessary in order to liberate the amine to use a further mole of the acid binding agent. The reaction is carried out in a suitable solvent, preferably at an elevated temperature, typically the reflux temperature of the solvent used. Examples of suitable solvents are ethers, for example dioxane, hydrocarbons, for example, benzene, toluene or xylene and ketones, for example acetone or methylisobutylketone. It may be advantageous to carry out the reaction under an inert atmosphere, for example under nitrogen.

Starting compounds of the general formula II, in which X signifies a halogen atom, can easily be produced from aminobenzophenones of the general formula IV

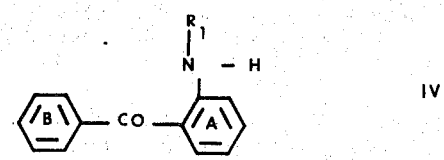

by reaction with a halogenacyl halide of the general formula V $$Hal-\overset{O}{\underset{\|}{C}}-C_nH_{2n}-Hal \qquad V$$

The initial compounds of the general formula II, in which X signifies the radical $R_2-NH-$, can be obtained by reacting a compound of the general formula IIa

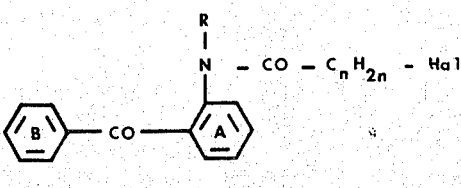

with an amine of the general formula VI $$R_2 - NH_2$$

The reaction is preferably carried out at a temperature between 5° and 50° with a reaction time of from a few hours up to several days, advantageously in a suitable solvent.

Those compounds of the general formula I, in which $m$ signifies 2 or 3 and $R_1$, $R_2$, $R_3$ and $n$ are as defined above, may be produced by an addition reaction between a benzophenone derivative of the general formula II, in which X signifies $R_2 - NH -$, and a compound containing an aliphatic double bond and of the general formula VII $$C_mH_{2m-1} - R_3 \qquad VII$$

in which $m$ means the number 2 or 3. The reaction is preferably carried out in a suitable solvent at room temperature or elevated temperature. Examples of suitable solvents are alcohols, ethers, ketones, hydrocarbons and acid amides.

Those compounds of the general formula I in which $R_3$ is CN and is in the $\alpha$ position in relation to the amino group of the side chain can also be prepared by reacting a compound of the general formula II, in which X signifies the radical $R_2$ — NH —, with an aldehyde or ketone of the general formula VIII $$C_mH_{2m}O \qquad \text{VIII}$$

and hydrocyanic acid or an alkali metal cyanide, preferably potassium cyanide. It is normally advantageous first to add the aldehyde or ketone of general formula VIII to an aqueous sodium bisulphite solution as in a Knoevenagel-Bucherer reaction, then to introduce the compound of general formula II, and finally a concentrated aqueous solution of alkali cyanide. The reaction is carried out at room temperature or slightly elevated temperature.

Normally compounds according to the invention are oily substances which provide crystalline acid addition salts.

The compounds of the general formula I and their pharmaceutically acceptable salts are characterised by valuable pharmacological properties, especially a pronounced sedative action on the central nervous system.

Some of these compounds also possess muscle-relaxing and aggression-inhibiting properties. The compounds of the general formula I and their pharmaceutically acceptable salts are therefore valuable pharmaceutical products which can be used as medicaments in the form of pharmaceutical preparations. The pharmaceutical preparations can be put up, for example, as tablets, suppositories, capsules, emulsions or suspensions in a known manner by the use of pharmaceutically acceptable diluents or carriers which do not react with the compounds. As diluents or carriers it is possible to use any substance which is suitable for the purpose in mind, for example talcum, starch, vegetable oils or petroleum jellies. If desired the pharmaceutical preparations may also contain other therepeutically active substance.

The pharmacological investigation of the sedative action on the central nervous system was carried out using the climbing test in albino mice described by P. K KNEIP: Arch. int. pharmacodyn 126, 238 (1960) and R. DOMENJOZ and W. THEOBALD: Arch. int. pharmacodyn 120, 450 (1959).

In the table which follows, the results of the pharmacological investigations carried out are summarised. In the last table under the heading "Sedative action %" there is given the percentage of the experimental animals which no longer take up the normally readily assumed climbing work.

| Compound | $LD_{50}$ g/kg (mouse) | | Dose mg/kg p.o. | Sedative action % |
|---|---|---|---|---|
| 2-(5-Cyano-N,4-dimethyl-3-aza-pentanamido)-5-chlor-benzophenone | 0.315 1.05 | i.p. p.o. | 4 | 40 |
| 2-(5-Cyano-3-aza-hexanamido)-5-chlor-benzophenone | 0.6 | i.p. | 8 | 50 |
| 2-(5-Cyano-N,3-dimethyl-3-aza-hexanamido)-5-nitro-benzophenone | 1.1 0.48 | p.o. i.p. | 1,6 | 50 |
| 2-(5-Cyano-N,4-dimethyl-3-aza-pentanamido)-benzophenone | 0.32 | i.p. | 8 | 70 |
| 2-(5-Cyano-3-allyl-3-aza-pentanamido)-2'-5-dichlor-benzophenone | 0.63 | i.p. | 8 | 60 |
| 2-(5-Cyano-N-methyl-3-n-butyl-3-aza-pentanamido)-5-chlor-benzophenone | 0.36 | i.p. | 8 | 80 |
| 2-(5-Cyano-N-methyl-3-n-butyl-3-aza-pentanamido)-5-nitro-benzophenone | 0.68 | i.p. | 8 | 50 |
| 2-(5-Cyano-N,4-dimethyl-3-aza-pentanamido)-5-methoxy-benzophenone | 0.25 | i.p. | 8 | 60 |
| 2-(5-Cyano-N,4-dimethyl-3-aza-pentanamido)-5-methyl-benzophenone | 0.3 | i.p. | 8 | 70 |
| 2-(4-Cyano-N-methyl-3-aza-butanamido)-5-chlor-benzophenone | 0.17 | i.p. | 8 | 60 |
| 2-(5-Cyano-N,3-dimethyl-3-aza-pentanamido)-5-chlor-benzophenone | 0.24 | i.p. | 8 | 80 |
| 2-(5-Cyano-N,3,4-trimethyl-3-aza-pentanamido)-5-chlor-benzophenone | 0.32 | i.p. | 9 | 50 |
| 2-(5-Cyano-N,3-dimethyl-3-aza-pentanamido)-5-nitro-benzophenone | >1.0 | p.o. | 10 | 50 |
| 2-(5-Cyano-4-methyl-3-aza-pentanamido)-benzophenone | >1.0 | p.o. | 10 | 50 |
| 2-(6-Cyano-3-methyl-3-aza hexanamido)-5-chlor-benzophenone | | | 8 | 60 |
| 2-(5-Cyano-N-methyl-3-aza-pentanamido)-5-methocy-benzophenone | | | 8 | 50 |
| 2-(5-Cyano-N-methyl-3-aza-pentanamido)-5-methyl-benzophenone | | | 8 | 50 |
| Comparative preparation Meprobamate | 0.62 | i.p. | 70 | 50 |

In the following examples the temperatures are given in °C. The abbreviation "Z" in the statements of the melting points means decomposition. The sorbent used for the thin layer chromatograms was silica gel HF 254 + 366 (Type 60) according to Stahl. The proportions given in the case of the eluents are proportions by volume.

EXAMPLE 1

9.8 g of 3-methylamino-2-methylpropionitrile were dissolved in 100 mls. of anhydrous dioxane. A weak stream of nitrogen was passed into this solution and it was heated to boiling under reflux. A solution of 16.1 g of 2-(2-chloro-N-methyl-acetamido)-5-chlorobenzophenone, dissolved in 150 mls. of anhydrous dioxane, was then added drop by drop whilst stirring, and the reaction mixture was heated under reflux for 4 hours. After cooling, the precipitated 3-methylamino-2-methylpropionitrile hydrochloride was filtered off under suction and the filtrate was concentrated in vacuo. The oily residue (20.0g) was dissolved in 300 mls. of absolute diethyl ether, filtered and the monohydrochloride of 2-(5-cyano-N,3-dimethyl-3-aza-hexanamido)-5-chlorobenzophenone was precipitated with dry hydrogen chloride. The yield was 18.8g, corresponding to 89% of theory. The product had a melting point of 113°–115° and was analytically pure without re-crystallisation. A thin-layer chromatogram of a sample of the product showed an absence of the starting compound and the RF value of the product was 0.85 in methanol.

EXAMPLE 2

3.2 g of 2-(methylamino-acetamido)-5-chlorobenzophenone hydrochloride, 0.75 g of chloracetonitrile and 2.0 g of triethylamine were heated with agitation under reflux for 8 hours in 100 mls. of absolute toluene. The triethylamine hydrochloride which was precipitated when the reaction mixture was cooled overnight was filtered off, and the filtrate was washed using 100 mls. of water each time, dried over potassium carbonate, filtered and concentrated in vacuo. The 3.5 g of oily base obtained were dissolved in 120 mls. of anhydrous ether, filtered and 2-(4-cyano-3-methyl-3-azabutyramido)-5-chlorobenzophenone hydrochloride with a melting point of 152°–154° was obtained in a yield of 3.2 g, corresponding to 84.5% of theory, by passing in dry hydrogen chloride. In a thin layer chromatogram the RF value in 2:8 cyclohexane/ethyl acetate as flow medium was 0.9.

EXAMPLE 3

3.3 g of 2-(2-Chloro-N-methyl-acetamido)-5-nitrobenzophenone, 1.2 g of 3-amino-butyronitrile hydrochloride and 2.0 g of triethylamine were heated in 100 mls. of anhydrous benzene for 4 hours while stirring and boiling under reflux. After cooling to room temperature the precipitated triethylamine hydrochloride was filtered off under suction and the filtrate was shaken three times with 100 mls. of water each time in a separating funnel, dried over potassium carbonate, filtered and concentrated in vacuo.

3.3 g of oily base obtained were dissolved in 150 mls. of anhydrous diethyl ether, the solution was filtered, and the monohydrochloride of 2-(5-cyano-N,4-dimethyl-3-aza-pentanamido)-5-nitro-benzophenone was obtained by passing dry hydrogen chloride into the solution. The yield was 2.9 g corresponding to 70% of theory, the melting point was 129°–131°, and the RF value in methanol as flow medium was 0.75.

By methods similar to those described in Examples 1, 2 and 3, the compounds set out in the following Table I were also synthesised:

TABLE I

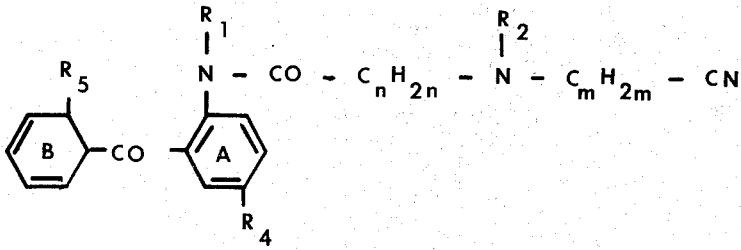

|   | $R_1$ | $C_nH_{2n}$ | $R_2$ | $C_mH_{2m}$ | $R_4$ | $R_5$ | Melting point of the hydrochloride |
|---|---|---|---|---|---|---|---|
| 1 | $CH_3$ | $-CH_2-$ | H | $-CH_2-CH_2-$ | Cl | H | 144 – 146° |
| 2 | $CH_3$ | $-CH_2-$ | H | $-CH_2-CH-$<br>$\quad\quad\;\;\;\mid$<br>$\quad\quad\;\;\;CH_3$ | Cl | H | 145 – 147° |
| 3 | $CH_3$ | $-CH_2-$ | H | $-CH-CH_2-$<br>$\;\;\;\mid$<br>$\;\;\;CH_3$ | Cl | H | 131 – 133° |
| 4 | $CH_3$ | $-CH_2-$ | H | $-CH_2-$ | Cl | H | 147 – 149° |
| 5 | H | $-CH_2-$ | H | $-CH_2-CH-$<br>$\quad\quad\;\;\;\mid$<br>$\quad\quad\;\;\;CH_3$ | Cl | H | 183 – 185° |
| 6 | H | $-CH_2-$ | H | $-CH-CH_2-$<br>$\;\;\;\mid$<br>$\;\;\;CH_3$ | Cl | H | 175 – 177° |
| 7 | $CH_3$ | $-CH_2-$ | $CH_3$ | $-CH_2-CH_2-$ | Cl | H | 184 – 186° |
| 8 | H | $-CH_2-$ | H | $-CH_2-CH_2-$ | Cl | H | 146 – 148° |
| 9 | H | $-CH_2-$ | $CH_3$ | $-CH_2-CH-$<br>$\quad\quad\;\;\;\mid$<br>$\quad\quad\;\;\;CH_3$ | Cl | H | 136 – 138° |

-continued

| | $R_1$ | $C_nH_{2n}$ | $R_2$ | $C_mH_{2m}$ | $R_4$ | $R_5$ | Melting point of the hydrochloride |
|---|---|---|---|---|---|---|---|
| 10 | H | —CH$_2$— | CH$_3$ | —CH$_2$—CH$_2$— | Cl | H | 165 – 167° |
| 11 | CH$_3$ | —CH$_2$— | CH$_3$ | —CH(CH$_3$)—CH$_2$— | Cl | H | 140 – 142° |
| 12 | CH$_3$ | —CH$_2$—CH$_2$— | H | —CH(CH$_3$)—CH$_2$— | Cl | H | 153 – 155° |
| 13 | CH$_3$ | —CH$_2$— | H | —CH$_2$—CH$_2$— | NO$_2$ | H | 119 – 121° |
| 14 | CH$_3$ | —CH$_2$— | CH$_3$ | —CH(CH$_3$)—CH$_2$— | NO$_2$ | H | 103 – 105° |
| 15 | CH$_3$ | —CH$_2$— | CH$_3$ | —CH$_2$—CH$_2$— | NO$_2$ | H | 80 – 82° |
| 16 | CH$_3$ | —CH$_2$— | CH$_2$—CH=CH$_2$ | —CH$_2$—CH$_2$— | Cl | H | 121 – 123° |
| 17 | CH$_3$ | —CH(CH$_3$)— | H | —CH(CH$_3$)—CH$_2$— | Cl | H | 126 – 128° |
| 18 | CH$_3$ | —CH$_2$— | CH$_3$ | —CH$_2$—CH(CH$_3$)— | NO$_2$ | H | 94 – 96° |
| 19 | CH$_3$ | —CH$_2$— | H | —CH$_2$— | NO$_2$ | H | 143 – 145° |
| 20 | H | —CH$_2$— | H | —CH(CH$_3$)—CH$_2$— | NO$_2$ | H | 200 – 202° |
| 21 | CH$_3$ | —CH$_2$—CH$_2$— | CH$_3$ | —CH$_2$—CH$_2$— | Cl | H | 149 – 152° |
| 22 | H | —CH$_2$— | H | —CH$_2$—CH$_2$— | NO$_2$ | H | 179 – 181° |
| 23 | CH$_3$ | —CH$_2$— | H | —CH(CH$_3$)—CH$_2$— | CF$_3$ | H | 113 – 115° |
| 24 | CH$_3$ | —CH$_2$— | H | —CH$_2$—CH$_2$— | CF$_3$ | H | 137 – 139° |
| 25 | CH$_3$ | —CH$_2$— | CH$_3$ | —CH(CH$_3$)—CH$_2$— | CF$_3$ | H | 145 – 148° |
| 26 | CH$_3$ | —CH$_2$— | H | —CH$_2$—CH(CH$_3$)— | CF$_3$ | H | 129 – 131° |
| 27 | H | —CH$_2$— | H | —CH(CH$_3$)—CH$_2$— | H | H | 132 – 134° |
| 28 | H | —CH$_2$— | H | —CH$_2$—CH$_2$— | CF$_3$ | H | 143 – 146° |
| 29 | CH$_3$ | —CH$_2$— | C$_2$H$_5$ | —CH(CH$_3$)—CH$_2$— | NO$_2$ | H | 106 – 109° |
| 30 | H | —CH$_2$— | H | —CH(CH$_3$)—CH$_2$— | Cl | Cl | 193 – 195° |
| 31 | CH$_3$ | —CH$_2$— | C$_2$H$_5$ | —CH$_2$—CH$_2$— | Cl | H | 128 – 130° |
| 32 | CH$_3$ | —CH$_2$—CH$_2$— | H | —CH(CH$_3$)—CH$_2$— | NO$_2$ | H | 174 – 176° |
| 33 | CH$_3$ | —CH$_2$—CH$_2$— | CH$_3$ | —CH$_2$—CH$_2$— | NO$_2$ | H | 177 – 179° |
| 34 | CH$_3$ | —CH$_2$— | H$_2$C—CH=CH$_2$ | —CH$_2$—CH$_2$— | NO$_2$ | H | 139 – 141° |
| 35 | CH$_3$ | —CH$_2$— | H$_2$C—CH=CH$_2$ | —CH$_2$—CH$_2$— | CF$_3$ | H | 94 – 96° (Z) |
| 36 | CH$_3$ | —CH$_2$— | H$_2$C—CH=CH$_2$ | —CH(CH$_3$)—CH$_2$— | Cl | H | 109 – 111° (Z) |
| 37 | CH$_3$ | —CH$_2$— | H$_2$C—CH=CH$_2$ | —CH(CH$_3$)—CH$_2$— | NO$_2$ | H | 102 – 104° (Z) |
| 38 | CH$_3$ | —CH$_2$— | H | —CH(CH$_3$)—CH$_2$— | H | H | 126 – 128° |
| 39 | CH$_3$ | —CH(CH$_3$)— | CH$_3$ | —CH$_2$—CH$_2$— | Cl | H | 151 – 153° |
| 40 | CH$_3$ | —CH(CH$_3$)—CH$_2$— | CH$_3$ | —CH$_2$—CH$_2$— | NO$_2$ | H | 97 – 100° |
| 41 | H | —CH$_2$— | H | —CH$_2$—CH$_2$— | Cl | Cl | 142 – 144° |
| 42 | H | —CH$_2$— | H$_2$C—CH=CH$_2$ | —CH$_2$—CH$_2$— | Cl | Cl | 128 – 130° |
| 43 | CH$_3$ | —CH$_2$— | CH$_3$ | —CH$_2$—CH$_2$—CH$_2$— | Cl | H | 143 – 145° |
| 44 | H | —CH$_2$— | CH$_3$ | —CH$_2$—CH$_2$—CH$_2$— | Cl | H | 164 – 167° (Z) |
| 45 | H$_2$C—CH=C-H$_2$ | —CH$_2$— | H | —CH(CH$_3$)—CH$_2$— | Cl | H | 125 – 127° |
| 46 | H$_2$C—CH=C-H$_2$ | —CH$_2$— | H$_2$C—CH=CH$_2$ | —CH$_2$—CH$_2$— | Cl | H | 128 – 130° |
| 47 | CH$_3$ | —CH$_2$— | n-C$_4$H$_9$ | —CH$_2$—CH$_2$— | Cl | H | 139 – 141° |
| 48 | CH$_3$ | —CH$_2$— | n-C$_4$H$_9$ | —CH$_2$—CH$_2$— | NO$_2$ | H | 127 – 129° |
| 49 | n-C$_4$H$_9$ | —CH$_2$— | H | —CH(CH$_3$)—CH$_2$— | Cl | H | 177 – 179° |
| 50 | n-C$_4$H$_9$ | —CH$_2$— | H | —CH$_2$—CH$_2$— | Cl | H | 163 – 165° (Z) |
| 51 | CH$_3$ | —CH$_2$— | H | —CH(CH$_3$)—CH$_2$— | OCH$_3$ | H | 136 – 138° |
| 52 | CH$_3$ | —CH$_2$— | H | —CH$_2$—CH$_2$— | OCH$_3$ | H | 154 – 156° |
| 53 | CH$_3$ | —CH$_2$— | H | —HC(CH$_3$)—CH$_2$— | SCH$_3$ | H | 134 – 136° |

| | $R_1$ | $C_nH_{2n}$ | $R_2$ | $C_mH_{2m}$ | $R_4$ | $R_5$ | Melting point of the hydrochloride |
|---|---|---|---|---|---|---|---|
| 54 | $CH_3$ | $-CH_2-$ | H | $-CH_2-CH_2-$ | $SCH_3$ | H | 145 – 147° (Z) |
| 55 | $CH_3$ | $-CH_2-$ | H | $-CH_2-CH_2-$ | $CH_3$ | H | 152 – 154° (Z) |
| 56 | $CH_3$ | $-CH_2-$ | H | $-CH(CH_3)-CH_2-$ | $CH_3$ | H | 143 – 145° |
| 57 | $CH_3$ | $-CH_2-$ | $C_2H_5$ | $-HC(CH_3)-CH_2-$ | $NO_2$ | H | 123 – 125° |
| 58 | $CH_3$ | $-CH_2-$ | $CH_3$ | $-HC(CH_3)-CH_2-$ | Cl | Cl | 152 – 155° (Z) |
| 59 | $CH_3$ | $-CH_2-$ | $CH_3$ | $-HC(CH_3)-CH_2-$ | Cl | F | 128 – 131° |
| 60 | $n\text{-}C_4H_9$ | $-CH_2-$ | $n\text{-}C_4H_9$ | $-CH_2-CH_2-$ | Cl | H | 119 – 121° |
| 61 | H | $-CH_2-$ | $n\text{-}C_4H_9$ | $-CH_2-CH_2-$ | Cl | Cl | 98 – 100° |

The production of starting compounds of the general formula II, in which X is chlorine or bromine, for use in the foregoing examples is exemplified by the production, described below, of the 2-(N-methyl-N-β-chloropropionylamino)-5-chloro-benzophenone used as starting compound for example in the production of 2-(6-cyano-N,5-dimethyl-4-aza-hexanamido)-5-chloro-benzophenone and 2-(6-cyano-N,4-dimethyl-4-aza-hexanamido)-5-chloro-benzophenone which appear in the table above, when they are produced according to the method of Example 4.

14.0 g of β-chloropropionyl chloride were rapidly added drop by drop to a solution of 24.6 g of 2-methylamino-5-chloro-benzophenone in 300 mls. of anhydrous toluene, the temperature rising from 18° to 25°C. The reaction mixture was then maintained for 4 hours at an internal temperature of 80°C, and then heated for a further 2 hours, with stirring, under reflux. After cooling, it is filtered and unreacted β-chloropropionyl chloride was drawn off under vacuum at approximately 0.1 mm Hg using a water bath rising to a final temperature of 90°C. The oily residue was allowed to stand for 3 days in a refrigerator where it crystallised. The crystals were rubbed up with petrol ether and dried in vacuo.

Yield: 29.8 g of 2-(N-methyl-N-β-chloro-propionylamino)-5-chloro-benzophenone (89% of theory) with a melting point of 73° – 75°.

EXAMPLE 4

3.0 g of 2-(methylamino-acetamido)-5-chloro-benzophenone were dissolved in 30 mls. of anhydrous alcohol and then mixed with 2.0 g of freshly distilled acrylonitrile. The mixture was stirred for 2 hours at room temperature and then heated under reflux for a further 8 hours. After being allowed to stand overnight at room temperature a further 2.0 g of freshly distilled acrylonitrile was added and the mixture heated under reflux with stirring for a further 4 hours. At this point a sample showed in a thin-layer chromatogram a uniform point which differed from that of the initial product. The turbid solution was filtered and concentrated in vacuo (approx. 0.1 mm Hg), 3.0 g of a colourless oil being obtained. This residue was dissolved in anhydrous diethyl ether. After passing dry hydrogen chloride into this solution, 3.6 g of 2-(5-cyano-3-methyl-3-aza-pentanamido)-5-chloro-benzophenone hydrochloride were obtained, corresponding to 92% of theory. The product had a melting point of 166°–168°. The RF value in a thin-layer chromatogram in methanol as flow medium was 0.85.

The RF value and the melting point were identical with those of the product which was obtained from 2-(chloracetamido)-5-chloro-benzophenone and β-methylamino-propionitrile using a method similar to that of Example 1 (cf. 10th example in table in Example 3).

The 2-(methylamino-acetamido)-5-chloro-benzophenone required as starting compound was produced as follows:

A solution of 24.5 g of 2-(chloracetamido)-5-chlorobenzophenone in 400 mls. of anhydrous dioxane was mixed with 150 mls. of a 15% solution of methylamine in methyl alcohol and was then allowed to stand at room temperature overnight in a closed vessel. The reaction mixture was then filtered and the filtrate is concentrated in vacuo at a waterbath temperature of 25°, the residue being shaken with 630 mls. of diethyl ether and 700 mls. of 0.3N hydrochloric acid. The ether layer was shaken out once again with 250 mls. of 0.3N hydrochloric acid and the combined hydrochloric acid extracts were rendered alkaline with concentrated aqueous ammonia whilst cooling thoroughly, and were then extracted with methylene chloride; the methylene chloride phase was dried over potassium carbonate. After drying, the methylene chloride solution was filtered and concentrated in vacuum. The oily crude base obtained as a residue, after drying, was dissolved in 100 mls. of anhydrous diethyl ether, filtered and converted by the introduction of dry hydrogen chloride into 23.8 g of 2-(methylamino-acetamido)-5-chlorobenzophenone hydrochloride (88% of theory), melting point 199°–201°.

EXAMPLE 5

2.1 g of sodium bisulphite were dissolved in 15 mls. of water and mixed drop by drop at 15°–20°C with 1.8 g of 40% formaldehyde solution, the stirring being continued for 30 minutes and then 3.0 g of 2-(methylamino-acetamido)-5-chloro-benzophenone were added to the reaction mixture. Then whilst stirring a solution of 1.3 g of potassium cyanide in 3 mls. of water was added drop by drop and the mixture stirred for 3 hours at 40°C. After being allowed to stand overnight at room temperature, the semi-solid reaction product was filtered off under suction, shaken up several times with water, and dried in a vacuum desiccator. From a solution of 2.4 g of the crude base in 100 mls. of anhydrous diethyl ether, 2.8 g of 2-(4-cyano-3-methyl-3-aza-butanamido)-5-chloro-benzophenone hydrochloride (74% of theory) with a melting point of 153°–155° were obtained by passing in dry hydrogen chloride.

The melting point and the RF value in a thin-layer chromatogram (0.9) correspond with those of the product obtained in Example 2.

EXAMPLE 6

In a three-necked flask equipped with a mechanically driven agitator and reflux condenser there were heated under reflux a mixture of 7.8 g 2-bromo-aceto-propargylamido-5-chloro-benzophenone (0.02 mole), 2.7 g 3-methyl-amino-2-methylproprionitrile-hydrochloride (0.02 mole) and 8 g triethylamine (0.04 mole + 100% in excess) in 300 mls. of anhydrous toluene for eight hours whilst stirring. After cooling, the precipitated triethylamine-hydrobromide and hydrochloride were filtered off with suction. The filtrate obtained was washed three times with 250 mls. of water each time. The organic phase which was dried over anhydrous potassium carbonate was filtered and evaporated in vacuo. The resultant oily crude base was vacuum-dried and after dissolving it in 400 mls. of dried diethylether, followed by filtration, dry hydrogen chloride was passed into the solution. The precipitate was filtered with suction and after drying it in vacuo, 7.4 g (83% of the theoretical) of 2-(5-cyano-N-propargyl-3.5-dimethyl-3-aza-pentanamido)-5-chloro-benzophenone-hydrochloride were obtained with a melting point of 144° to 146°. When administering a dose of 8.0 mg./kg., the sedative action on the central nervous system was 50%.

Analogously, there were obtained:

2-(5-cyano-N-propargyl-3-aza-4-methyl-pentanamido)-5-chloro-benzophenone-hydrochloride melting at 129° to 131°. When administering a dose of 16.0 mg./kg. the aggression-inhibiting action was 71%.

EXAMPLE 7

A mixture consisting of 4.7 g of 2-bromoaceto-β-bromallylamido-5-chloro-benzophenone (0.01 mole), 1.0 g. of 3-methylamino-2-methyl-propionitrile (0.01 mole) and 1 g. of triethylamine (0.01 mole) was heated in 150 mls. of anhydrous toluene at an internal temperature of 80° for eight hours whilst stirring. After cooling, the precipitated triethylamine-hydrobromide was filtered with suction and the filtrate obtained washed three times with 150 mls. of water each time. After drying it over anhydrous potassium carbonate, the organic phase was filtered and evaporated in the vacuum. The oily crude base so obtained was vacuum-dried. After dissolving the latter in 200 ml. anhydrous diethylether, followed by filtration, dry hydrogen-chloride was passed into the solution. The precipitate being filtered with suction and vacuum-dried, there were obtained 4.1 g. (78% of the theoretical) of 2-(5-cyano-N-β-bromoallyl-3,5-dimethyl-3-aza-pentanamido)-5-chlorobenzophenone-hydrochloride having a melting point of 141° to 143°.

Analogously, there were obtained:

2-(5-cyano-N-β-bromoallyl-4-methyl-3-aza-pentanamido)-5-chloro-benzophenone-hydrochloride melting at 133° to 135°.

By methods analogous to those described in Examples 1 and 2 the compounds listed in the following Table II were synthesized:

Table II

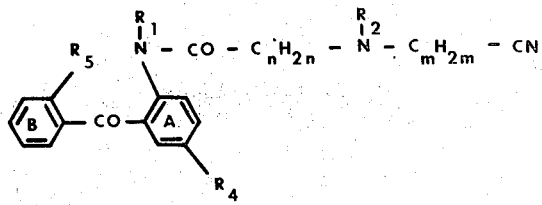

| $R_1$ | $C_nH_{2n}$ | $R_2$ | $C_mH_{2m}$ | $R_4$ | $R_5$ | Melting point of the hydrochloride |
|---|---|---|---|---|---|---|
| $CH_3$ | $-CH_2-$ | $CH_3$ | $-CH_2-CH-$<br>$\quad\quad\quad CH_3$ | $NO_2$ | Cl | 246–248° |
| $CH_3$ | $-CH_2-$ | H | $-CH-CH_2-$<br>$\ CH_3$ | $NO_2$ | Cl | 239–241° |
| $CH(CH_3)_2$ | $-CH_2$ | $CH_3$ | $-CH_2-CH-$<br>$\quad\quad\quad CH_3$ | H | H | 135–138° |
| $CH(CH_3)_2$ | $-CH_2$ | H | $-CH-CH_2-$<br>$\ CH_3$ | H | H | 100–102° |
| $CH(CH_3)_2$ | $-CH_2-$ | $CH_3$ | $-CH_2-CH-$<br>$\quad\quad\quad CH_3$ | Cl | H | 195–198° |
| $CH_3$ | $-CH_2-$ | (n)$(CH_2)_4-CH_3$ | $-CH_2-CH_2-$ | Cl | H | 90–93° |
| $CH_3$ | $-CH_2-$ | $CH-C_2H_5$<br>$\ CH_3$ | $-CH_2-CH_2-$ | Cl | H | 77–78° (Z.) |
| $CH_3$ | $-CH_2-$ | $CH-C_2H_5$<br>$\ CH_3$ | $-CH_2-CH_2-$ | $NO_2$ | H | 128–130° |
| $CH_3$ | $-CH_2-$ | H | $-CH-CH_2-$<br>$\ CH_3$ | Cl | F | 136–138° |
| $CH_3$ | $-CH_2-$ | $CH_3$ | $-CH_2-CH-$<br>$\quad\quad\quad CH_3$ | Cl | F | 188–190° |
| $CH_3$ | $-CH_2-$ | $CH_3$ | $-CH_2-CH-$<br>$\quad\quad\quad CH_3$ | Cl | Cl | 136–138° |

-continued

| $R_1$ | $C_nH_{2n}$ | $R_2$ | $C_mH_{2m}$ | $R_4$ | $R_5$ | Melting point of the hydrochloride |
|---|---|---|---|---|---|---|
| $CH_3$ | $-CH_2-$ | $(n)C_4H_9$ | $-CH_2-CH_2-$ | Cl | Cl | 98–100° |
| $CH_3$ | $-CH_2-$ | H | $-CH(CH_3)-CH_2-$ | Cl | Cl | 125–128° |
| $CH_3$ | $-CH_2-$ | $CH_3$ | $-CH(CH_3)-CH_2-$ | H | H | 106–108° |
| $CH_3$ | $-CH_2-$ | $(n)C_4H_9$ | $-CH_2-CH_2-$ | H | H | 96–98° |
| $CH_3$ | $-CH_2-$ | $(n)C_4H_9$ | $-CH(CH_3)-CH_2-$ | H | H | 76–78° (Z.) |
| $CH_3$ | $-CH_2-$ | $CH_3$ | $-CH_2-CH_2-CH_2-$ | $CH_3$ | H | 123–125° |
| $CH_3$ | $-CH_2-$ | $CH_3$ | $-CH_2-CH_2-CH_2-$ | $OCH_3$ | H | 118–120° |
| $CH_3$ | $-CH_2-$ | $CH_3$ | $-CH_2-CH_2-CH_2-$ | $NO_2$ | H | 120–122° (Z.) |
| $CH_3$ | $-CH_2-$ | $(n)C_4H_9$ | $-CH(CH_3)-CH_2-$ | Cl | H | 120–122° |
| $CH_3$ | $-CH_2-$ | $(n)C_4H_9$ | $-CH_2-CH(CH_3)-$ | Cl | H | 109–111° |
| $(n)C_4H_9$ | $-CH_2-$ | $CH_3$ | $-CH_2-CH(CH_3)-$ | Cl | H | 121–124° |
| $CH_3$ | $-CH_2-$ | $(n)C_4H_9$ | $-CH_2-CH_2-$ | $OCH_3$ | H | 116–118° |
| $CH_3$ | $-CH_2-$ | $CH_3$ | $-CH(CH_3)-CH_2-$ | $OCH_3$ | H | 152–154° |
| $CH_3$ | $-CH_2-$ | $CH_3$ | $-CH(CH_3)-CH_2-$ | $SCH_3$ | H | 128–130° |
| $CH_3$ | $-CH_2-$ | $(n)C_4H_9$ | $-CH_2-CH_2-$ | $CH_3$ | H | 140–142° |
| $CH_3$ | $-CH_2-$ | $CH_3$ | $-CH(CH_3)-CH_2-$ | $CH_3$ | H | 124–126° |

The pharmacological investigation of the muscle-relaxing action was carried out using the rotarod-method on albino mice described by W. J. Kinnard Jr. and C. J. Carr, Journal of Pharmacology and Experimental Therapeutics, Vol. 121, 355 (1957).

The percentages specified for the muscle-relaxing action represent the percentage animals on test which were still sitting on the rotating rod at the end of the test.

The pharmacological investigation of the aggression-inhibiting properties was carried out using the fighting test of albino mice described by R. E. Tedeschi, D. H., R. E. Tedeschi, A. Mucha, L. Cook, P. A. Mattis and E. J. Fellows, Journal of Pharmacology and Experimental Therapeutics, Vol. 125, 28–29 (1959).

The percentages specified for the aggression-inhibiting properties represent the percentage by which the fighting activity of the test animals has diminished.

In the Table III which follows, the results of further pharmacological investigations carried out are summarized.

Table III

| Compound | Muscle-relaxing action | | Sedative action | | Aggression-inhibiting action | |
|---|---|---|---|---|---|---|
| | mg/kg p.o. | % | mg/kg p.o. | % | mg/kg p.o. | % |
| 2-(5-cyano-N-methyl-3-n-amyl-3-aza-pentanamido)-5-chlor-benzophenone | 5,5 | 40 | 8,0 | 60 | — | — |
| 2-(5-cyano-N-3,4-trimethyl-3-aza-pentanamido)-5-chlor-2'-fluor-benzophenone | 4,0 | 100 | 2,5 | 50 | 4,0 | 89 |
| 2-(5-cyano-3-aza-pentanamido)-2'-5-dichlor-benzophenone | 5,5 | 100 | 2,5 | 90 | — | — |
| 2-(5-cyano-N,3,4-trimethyl-3-aza-pentanamido)-2',5-dichlor-benzophenone | 4,0 | 80 | 2,5 | 80 | 10,0 | 83 |
| 2-(5-cyano-N,3,-dimethyl-3-aza-hexanamido)-2',5-dichlor-benzophenone | 5,5 | 100 | 8,0 | 100 | 16,0 | 88 |
| 2-(5-cyano-N-methyl-3-(n)butyl-3-aza-pentanamido)-2',5-dichlor-benzophenone | 5,5 | 70 | 8,0 | 70 | 16,0 | 67 |
| 2-(5-cyano-N,4-dimethyl-3-(n)butyl-3-aza-pentanamido)-5-chlor-benzophenone | 5,5 | 30 | 8,0 | 70 | 16,0 | 37 |
| 2-(5-cyano-N,5-dimethyl-3-(n)butyl-3-aza-pentanamido)-5-chlor-benzophenone | 5,5 | 40 | 8,0 | 60 | 16,0 | 54 |
| 2-(5-cyano-N(n)-butyl-3,5-dimethyl-3-aza-pentanamido)-5-chlor-benzophenone | 5,5 | 30 | 8,0 | 60 | 16,0 | 58 |

Table III-continued

| Compound | Muscle-relaxing action | | Sedative action | | Aggression-inhibiting action | |
|---|---|---|---|---|---|---|
| | mg/kg p.o. | % | mg/kg p.o. | % | mg/kg p.o. | % |
| 2-(5-cyano-N,3,4-trimethyl-3-aza-pentanamido)-5-methoxy-benzophenone | 5,5 | 0 | 8,0 | 50 | 16,0 | 42 |
| 2-(5-cyano-N,3,4-trimethyl-3-aza-pentanamido)-5-methyl-benzophenone | 5,5 | 0 | 8,0 | 20 | 16,0 | 53 |
| 2-(5-cyano-N,4-dimethyl-3-aza-pentanamido)-5-nitro-benzophenone | 5,0 | 50 | 10,0 | 30 | 16,0 | 84 |
| 2-(5-cyano-N,3,4-trimethyl-3-aza-pentanamido)-5-nitro-benzophenone | 5,0 | 90 | 10,0 | 20 | 16,0 | 87 |
| 2-(5-cyano-4-methyl-3-aza-pentanamido)-5-nitro-benzophenone | 5,0 | 0 | 10,0 | 30 | 16,0 | 60 |
| 2-(5-cyano-N,3,4-trimethyl-3-aza-pentanamido)-5-trifluor-methyl-benzophenone | 5,0 | 80 | 10,0 | 40 | 16,0 | 59 |
| 2-(5-cyano-N-methyl-3-allyl-3-aza-pentanamido)-5-chlor-benzophenone | 5,0 | 100 | 10,0 | 40 | — | — |
| 2-(5-cyano-N,3-dimethyl-3-aza-pentanamido)-5-chlor-benzophenone | 5,5 | 60 | 8,0 | 80 | — | — |
| 2-(5-cyano-N,3-dimethyl-3-aza-pentanamido)-5-nitro-benzophenone | 5,0 | 100 | 10,0 | 50 | — | — |
| 2-(5-cyano-N,4-dimethyl-3-athyl-3-aza-pentanamido)-5-nitro-benzophenone | 4,0 | 70 | 2,5 | 40 | — | — |
| 2-(5-cyano-N,4-dimethyl-3-aza-pentanamido)-5-chlor-benzophenone | 4,0 | 90 | 4,0 | 40 | 10,0 | 39 |
| 2-(5-cyano-N,3-dimethyl-3-aza-hexanamido)-5-nitro-benzophenone | 4,0 | 90 | 1,6 | 50 | 4,0 | 41 |
| Comparative preparation meprobamate | 50 | 50 | 70 | 50 | 120 i.p. | 50 |

Legend:
0 signifies no action
— no tests carried out

Preferred compounds according to the present invention are those in which $R_1$ is selected from the group consisting of hydrogen, alkyl having from 1 to 4 carbon atoms, allyl, β-bromoallyl and propargyl, $R_2$ is selected from the group consisting of hydrogen, allyl having from 1 to 5 carbon atoms and allyl, $n$ is 1 or 2, $m$ is 1, 2 or 3, the ring A is selected from the group consisting of phenylene-(1,2); 5-chlorophenylene -(1,2); 5-methyl-phenylene-(1,2); 5-methoxyphenylene-(1,2); 5-methylmercaptophenylene-(1,2); 5-nitrophenylene -(1,2); 5-trifluoromethylphenylene -(1,2); the ring B is selected from the group consisting of phenyl, 2'-fluorophenyl; 2'-chlorophenyl;

Particularly preferred $R_1$ and $R_2$ radicals are those in which $R_1$ is selected from the group consisting of hydrogen, methyl, ethyl, propargyl, $R_2$ is selected from the group consisting of hydrogen, methyl, allyl, n-butyl.

The compounds according to the invention can be converted in the usual manner to crystalline acid addition salts.

Pharmaceutically acceptable acid addition salts include hydrochlorides, hydrobromides, sulphates, phosphates, lactates, maleates, malates, fumarates, oxalates, glycolates, citrates, tartrates and acetates.

What is claimed is:

1. Benzophenone derivatives having the structural formula

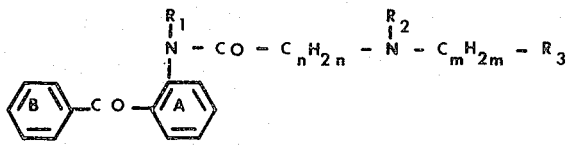

and the acid addition salts thereof, wherein $R_1$ and $R_2$ are substituents selected from the group consisting of hydrogen, alkyl having 1 to 5 carbon atoms, an alkenyl radical with 2 to 4 carbon atoms, an alkinyl radical with 2 to 4 carbon atoms, or a β-bromoallyl radical ($-CH_2-CBr=CH_2$); $R_3$ is CN; $n$ is an integer selected from 1 and 2; and $m$ is an integer selected from 1, 2 and 3, and wherein the ring A is selected from the group consisting of phenylene, halogenphenylene, nitrophenylene, trifluormethylphenylene, methylphenylene, methoxyphenylene and methylmercaptophenylene; the ring B is selected from the group consisting of phenyl, fluorphenyl and chlorophenyl.

2. Benzophenone derivatives according to claim 1, wherein the ring A is substituted at the 5-position and the ring B is substituted at the 2'-position.

3. Benzophenone derivatives according to claim 1, wherein $R_1$ is selected from the group consisting of hydrogen, having from 1 to 4 carbon atoms, allyl, β-bromoallyl and propargyl, $R_2$ is selected from the group consisting of hydrogen, alkyl having from 1 to 5 carbon atoms and allyl.

4. 2-(5-cyano-N-3,4-trimethyl-3-aza-pentanamido)-5-chloro-2'-fluoro-benzophenone and pharmaceutically acceptable acid addition salts thereof.

5. 2-(5-cyano-N,3,4-trimethyl-3-aza-pentanamido)-2',5-dichloro-benzophenone and pharmaceutically acceptable acid addition salts thereof.

6. 2-(5-cyano-N,3,-dimethyl-3-aza-hexanamido)-2',5-dichloro-benzophenone and pharmaceutically acceptable acid addition salts thereof.

7. 2-(5-cyano-N-methyl-3-(n)butyl-3-aza-pentanamido)-2',5-dichloro-benzophenone and pharmaceutically acceptable acid addition salts thereof.

8. 2-(5-cyano-N,3,4-trimethyl-3-aza-pentanamido)-5-nitro-benzophenone and pharmaceutically acceptable acid addition salts thereof.

* * * * *